United States Patent
Hasseberg et al.

[11] Patent Number: 6,146,612
[45] Date of Patent: Nov. 14, 2000

[54] METHOD FOR RECOVERING SULFURIC ACID FROM SULFATE SALTS

[75] Inventors: Hans Albrecht Hasseberg, Grundau; Hans Joachim Hasselbach; Klaus Huthmacher, both of Gelnhausen; Volker Hafner, Langenselbold; Harald Heinzel, Frankfurt, all of Germany

[73] Assignee: Degussa-Huls AG, Frankfurt am Main, Germany

[21] Appl. No.: 09/206,948

[22] Filed: Dec. 8, 1998

[30] Foreign Application Priority Data

Dec. 9, 1997 [DE] Germany ............................ 197 54 562

[51] Int. Cl.$^7$ .................................................. C01B 17/74
[52] U.S. Cl. ...................... 423/522; 423/523; 423/530; 423/541.1; 423/542; 423/243.01
[58] Field of Search ................. 423/243.01, 530, 423/532, 541.1, 522, 523, 541.4, 542

[56] References Cited

U.S. PATENT DOCUMENTS

| | | | |
|---|---|---|---|
| 3,733,393 | 5/1973 | Couillaud | 423/215 |
| 3,760,061 | 9/1973 | Hammond | 423/242 |
| 4,912,257 | 3/1990 | Hernandez et al. | 562/581 |
| 5,498,790 | 3/1996 | Grendel et al. | 562/581 |
| 5,595,713 | 1/1997 | Gohara | 422/170 |
| 5,847,207 | 12/1998 | Suchsland et al. | 562/581 |
| 5,976,609 | 11/1999 | Hasseberg et al. | 426/648 |

FOREIGN PATENT DOCUMENTS

| | | | |
|---|---|---|---|
| 2 304 784 | 8/1973 | Germany | 423/243.01 |
| 24 45 598 | 3/1975 | Germany | 423/243.01 |
| 40 36 899 A1 | 5/1992 | Germany . | |

OTHER PUBLICATIONS

English Abstract for DE 40 36 899 A, May 21, 1992.

*Primary Examiner*—Steven P. Griffin
*Assistant Examiner*—Timothy C Vanoy
*Attorney, Agent, or Firm*—Pillsbury Madison & Sutro LLP

[57] ABSTRACT

A process is provided for the recovery of sulfuric acid from $NH_4HSO_4$ and $(NH_4)_2SO_4$ salts produced from the sulfuric acid hydrolysis of methylmercaptopropionaldehyde (MMP) cyanohydrin to produce 2-hydroxy-4-methylthiobutyric acid (MHA), which can be used as an additive in animal feed. The sulfate salts are combusted in a furnace to produce sulfur dioxide; the sulfur dioxide is contacted with an aqueous solution containing sulfuric acid and hydrogen peroxide, where the sulfur dioxide is converted into sulfuric acid. The product sulfuric acid is recovered.

11 Claims, 3 Drawing Sheets

METHOD FOR RECOVERING SULFURIC ACID FROM SULFATE SALTS

FIELD OF THE INVENTION

The invention relates to a method for recovering sulfuric acid from by-products containing sulfate which arise in processes for preparing 2-hydroxy-4-methylthiobutyric acid (MHA), wherein the sulfuric acid accumulates in a grade in which it can be directly re-employed in such processes.

MHA is the hydroxy analogue of the essential amino acid methionine in racemic form and can be employed as an additive in feedstuffs, in particular for the rearing of poultry, but also in many other fields, particularly in the form of its aqueous concentrates.

BACKGROUND OF THE INVENTION

The synthesis pathway that is used exclusively in technical applications starts out from methylmercaptopropionaldehyde (MMP) which by addition of HCN is converted into the corresponding cyanohydrin (MMP-CH) which is then firstly catalyzed with sulfuric solution to form MHA amide and in a further step is hydrolyzed to form the hydroxy acid MHA, the sulfuric acid being converted into ammonium hydrogensulfate and, optionally, ammonium sulfate.

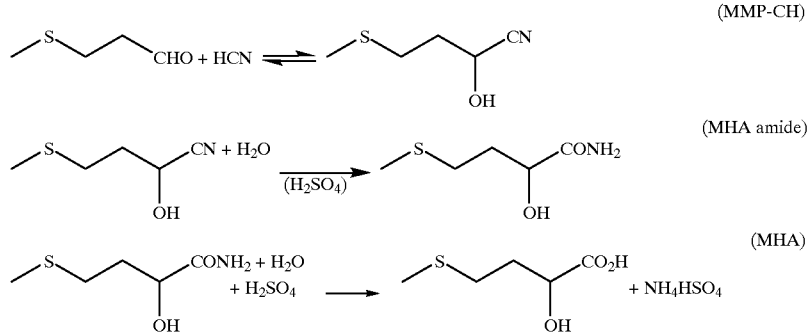

(MMP-CH)

(MHA amide)

(MHA)

Starting from MHA hydrolysate, which consequently contains, in addition to corresponding portions of water, ammonium hydrogensulfate/sulfate, there are various methods for isolating MHA, which are described in summary form in German published application DE-OS 19 524 054 and in DE-PS 4 428 608.

These methods involve either solvent extraction or precipitation steps or a combination of both for the purpose of separating MHA from the salt that has been formed at the same time.

With each of these processes, in addition to the product MHA a portion of ammonium hydrogensulfate/sulfate corresponding to the quantity of sulfuric acid previously introduced is produced in the form of a solution or in a more or less pure solid grade. Since production of MHA is of the order of about 20,000 to 300,000 tons per annun per plant, quantities of sulfate salt also accumulate in quantities of approximately the same magnitude, which hitherto had to be disposed of in an expensive manner or dumped. However, in particular the dumping of such gigantic quantities of salt is unjustifiable from the ecological point of view and is also not economically sensible as a result of further increasing charges. With a view to utilizing the waste salts it is therefore particularly desirable to recover sulfuric acid from the sulfates and to return the sulfuric acid into the MHA process.

A quite similar composite method is already known from the technical process for preparing methyl methacrylate (MMA), as described, for example, in U.S. Pat. No. 3,549,320. In this case acetone cyanohydrin is first converted with, sulfuric acid into methacrylamide sulfate and subsequently with methanol into methyl methacrylate and ammonium bisulfate. After separation of the MMA, the residue containing sulfuric acid and ammonium bisulfate is transformed into sulfuric acid in a cracking contact plant. This method, which is known from the state of the art, is proposed in U.S. Pat. No. 5,498,790 with a view to the utilization of waste salt in the MHA process. In this connection the raffinate solution arising from the MHA extraction, principally containing ammonium bisulfate or ammonium sulfate, water and small quantities of organic by-products, is firstly subjected to combustion in a cracking furnace together with a fuel at about 900 to 1,200° C. to form $SO_2$, $N_2$, $O_2$, $CO_2$ and $H_2O$:

$$2NH_4HSO_4 + \tfrac{1}{2}O_2 \rightarrow N_2 + 2SO_2 + 5H_2O$$

After cooling to 35°–45° C. with a view to condensation of portions of water and subsequent reheating together with oxygen, the hot combustion gas containing $SO_2$ is conducted into a contact furnace and the $SO_2$ is oxidized there on the $V_2O_5$ contact substance at temperatures of at least 420° C. to form $SO_3$:

$$SO_2 + \tfrac{1}{2}O_2 \rightarrow SO_3.$$

However, the economic implementation of this method is tied to minimum concentrations of $SO_2$.

The contact gas containing sulfur trioxide is absorbed in oleum in accordance with a long-established procedure and, as a result of subsequent dilution with water, sulfuric acid is produced having a concentration of about 65 wt % that is needed for the MHA process.

The disadvantages of this method which is described in U.S. Pat. No. 5,498,790 consist in the elaborate and complicated process technology for the contact furnace, wherein the stream of cracking gas containing $SO_2$ has to be conducted with oxygen over several contact trays and, after intermediate absorption of the $SO_3$ which has already formed, conversion of the remaining sulfur dioxide is brought about on the last tray by intermediate cooling and reheating to the reaction temperature.

Further disadvantages are the high reaction temperature of over 420° C., which in addition is attained by reheating the $SO_2$ combustion gas which has cooled down to 35°–45° C., and also the non-quantitative conversion of the $SO_2$ portion in the course of catalytic oxidation in the contact furnace, which results in a residual $SO_2$ content in the waste gas leaving the contact furnace. This portion has to be lowered to the permitted legal limits by means of a suitable aftertreatment. The method described in U.S. Pat. No. 5,498,790 preferably operates with a minimum concentration of 70 wt % of sulfate salt in the input stream of the combustion furnace, since a lower concentration results in an additional demand for fuel for evaporation of the high proportion of water and in higher inert-gas portions consisting of $CO_2$, $N_2$ etc. In this case the $SO_2$ concentration falls so considerably that the contact furnace can no longer be operated effectively. In particular, solutions containing ammonium as described in U.S. Pat. No. 4,912,257, the maximum sulfate concentration of which is clearly below 70 wt %, can be introduced in the form of a suspension only after further concentration. In operation this leads to greater difficulties such as blockages, for example, and is consequently not very practicable (cf. U.S. Pat. No. 5,498,790, bottom of col. 14 and top of col. 15).

Further disadvantages consist in the use of a heavy-metal catalyst that is tied to sufficiently high concentrations of $SO_2$, and the risk resulting therefrom of contamination of the product with catalyst residues and also with $NO_x$ which can be formed as a result of catalytic oxidation at the stated reaction temperatures. In the course of returning the sulfuric acid into the MHA process these contaminants may find their way into the MHA end product which is employed as feedstuff additive. By their nature they are undesirable therein.

SUMMARY OF THE INVENTION

The object of the invention is to make available a simpler method for recovering sulfuric acid from by-products containing sulfate that arise from the preparation of MHA, with the aid of which method, under conditions that are as mild as possible and without contamination by heavy metals and $NO_x$, a grade of sulfuric acid is obtained that can be directly re-employed in the hydrolysis stage of a process for the preparation of MHA. The method is furthermore to be capable of being employed irrespective of the $SO_2$ concentration of the combustion gases and, after the production of sulfuric acid, is to yield a waste gas that can be emitted into the atmosphere without further aftertreatment.

The invention provides a method for recovering sulfuric acid from solutions or solids containing sulfate that accumulate in the course of the sulfuric hydrolysis of MMP cyanohydrin, wherein the sulfates are converted in a combustion furnace into $SO_2$, said method being characterized in that the gas mixture containing $SO_2$ is passed through an aqueous sulfuric solution of $H_2O_2$ and is converted into sulfuric acid in accordance with the following overall equation:

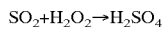

In this process it is possible to produce sulfuric acid in a concentration and in a grade that can be directly employed for the preparation of MHA by hydrolysis of MMP cyanohydrin.

No detectable $NO_x$ contaminant can be found in the sulfuric acid prepared in accordance with the invention, so this sulfuric acid can be employed for the hydrolysis step without problems.

According to the invention the procedure is preferably such that the combustion gas containing $SO_2$ is passed at a temperature between 0° and 100° C., preferably between 10° and 80° C., and more preferably 20° to 60° C., through a packed column in which an acidic aqueous solution of hydrogen peroxide is located, which is circulated. Hydrogen peroxide is preferably employed having a concentration between 10 and 90 wt %, preferably between 20 and 80 wt %, and more preferably between 30 and 60 wt %, with the proviso that consumed hydrogen peroxide corresponding to the quantities of $SO_2$ in the desired or necessary concentration is made up by further metering.

As is a matter of course, to a person skilled in the art, the gas containing $SO_2$ is simultaneously cooled in this device and/or prior to entering this device.

As in a conventional manner of working, a simple packed column is employed for the purpose of absorbing the sulfur dioxide. The packed column is generally operated in the form of a cooled absorption circuit. At least two-stage absorption in one of the absorption columns that are known for these purposes is to be regarded as a preferred embodiment.

The procedure is advantageously such that the combustion gas containing $SO_2$ is introduced into the column in the vicinity of the sump. The column packing is optionally circulated repeatedly.

In a preferred embodiment, the recycled liquid is brought into contact with the gas containing $SO_2$ until such time as practically no $H_2O_2$ is present any longer in the solution in the circuit.

The desired $H_2SO_4$ concentration is adjusted via the $H_2O_2$ concentration of the hydrogen-peroxide solution employed. This is between 10 and 90 wt %, preferably between 20 and 80 wt %, and most preferably between 30 and 60 wt %.

According to the invention, working preferably takes place in such a way that a maximum sulfuric acid concentration of 50 to 78 wt % is attained.

In an advantageous embodiment, the sulfuric acid that has been produced in this way is continuously discharged from the optionally multi-stage reactor.

Depending on the $SO_2$ concentration in the combustion gas, differing quantities of $H_2SO_4$ per unit of time are produced for a given volumetric flow of the combustion gas.

In one technical embodiment it is advisable to employ a two-stage apparatus that consists of two absorption circuits (cf. FIG. 2), the first absorption circuit being operated with a molar deficit of $H_2O_2$ with respect to the $SO_2$ portion in the combustion gas introduced therein and the second absorption circuit being operated with an excess of $H_2O_2$. The partly oxidized gas stream discharged from the first circuit is supplied to the second circuit and the $SO_2$ residue is converted therein. To this end the second circuit is charged with fresh $H_2O_2$ in a molar excess relative to the $SO_2$ portion that is fed in there. The sulfuric acid with residual $H_2O_2$ content that is located in the second circuit is continuously discharged with a view to supplying the first circuit and therein the remaining $H_2O_2$ from the second circuit is caused to react completely with the crude gas. $H_2O_2$-free sulfuric acid having the appropriately adjusted concentration is continuously obtained from the first circuit as recycling product.

An insignificant proportion of $H_2SO_3$ which may possibly be contained in the sulfuric acid produced in this way, arising from unreacted $SO_2$, is not critical for the intended purpose of hydrolysis of MMP cyanohydrin to form MHA, because no side reactions of any kind can be caused thereby.

In a particularly elegant manner it is possible for such regeneration of $H_2SO_4$ and recycling to be achieved within an appropriate cyclic process in which the sulfuric acid can be returned into the stage for sulfuric hydrolysis of MMP-CH to form MHA amide (cf. FIG. 3).

Furthermore, with a view to producing $SO_2$ in the combustion furnace it is readily possible to make use of additional sulfur sources besides the sulfates from an MHA process. On the one hand, elemental sulfur can be directly subjected to combustion, which is sensible in particular in the case of increased demand for sulfuric acid. On the other hand, however, sulfates from other processes can also be used in the same way. To be considered in this connection are, in particular, wash solutions containing $NH_4HSO_4$ or $(NH_4)_2SO_4$, arising for example from a hydrocyanic acid process. In such a process the residual $NH_3$ in washers is washed out with aqueous sulfuric acid in the course of the production of HCN from $CH_4$ and $NH_3$. The solutions containing sulfate that are produced in this way can be directly utilized in a combustion furnace, irrespective of their concentration. In the subsequent $H_2O_2$-oxidation stage sulfuric acid is again produced therefrom which can be returned into the HCN process.

Since HCN is consumed for the purpose of producing MMP cyanohydrin and since, by reason of the fact that transfers of hydrocyanic acid are only possible to a limited extent for reasons of safety, as a general rule an appropriate HCN plant has to be situated in the immediate vicinity of an MHA plant, here too a direct composite process is possible. The latter is exceptionally advantageous from economic and ecological points of view and also from the point of view of modern safety engineering.

Strong-smelling sulfurous waste waters or waste gases such as typically accumulate, in addition to sulfate, in an MHA process but which may also originate from other plants, preferably at the same location, can also be utilized similarly in the combustion furnace.

Here, in contrast to the catalytic atmospheric oxidation of combustion gas containing $SO_2$ at >420° C. which is described in U.S. Pat. No. 5,498,790, the amount of gas ballast produced at the same time by virtue of increased inert portions or excess consumption of fuel in the course of combustion of dilute solutions is totally irrelevant. In the $H_2O_2$ oxidation, used in accordance with the invention, of such a combustion gas, arbitrarily low $SO_2$ concentrations can also be transformed quantitatively into sulfuric acid with hydrogen peroxide, as is known from corresponding methods for waste-gas desulfurization. In contrast with the method according to U.S. Pat. No. 5,498,790 there is no minimum requirement for the sulfate or sulfur concentration in the input stream to the combustion furnace.

The combustion gas containing $SO_2$ that has cooled down to <50° C. may in addition be supplied directly to the $H_2O_2$-oxidation stage without reheating. Separation of $SO_3$ which is already present proportionately, as is necessary in the case of the catalytic process, can likewise be dispensed with here.

The claimed method is distinguished in particular by the fact that it avoids waste streams and the sulfuric acid employed for the purpose of hydrolysis can be completely recovered. Even defective charges containing MHA can be introduced as fuel into the combustion furnace. The sulfur contained therein is converted into sulfur dioxide which, in accordance with the invention, is converted with $H_2O_2$ into sulfuric acid.

This application is based on German patent application DE 19754562.9, filed Dec. 9, 1997, the disclosure of which is incorporated herein by reference.

DETAILED DESCRIPTION OF THE PREFERRED EMBODIMENTS

The following preparative Examples serve to clarify the subject of the invention further:

Analytical Methods of Determination and Definitions

The contents of MHA monomer and of MHA amide were determined quantitatively in the process solutions by HPLC by comparison with an external standard (pure substance).

The content of total MHA (MHAtot)=MHA monomer+ MHA (dimers+oligomers)+MHA amide (optionally) is determined by titrimetric determination of the thioether function with $KBr/KBrO_3$ standard solution and was expressed as the sum of the corresponding MHA monomer equivalents in [wt %] or [g] or [mole] or [mole %].

The content of MHA dimers+MHA oligomers (DIM+ OLI) was ascertained by calculating the difference of total MHA and MHA monomer+MHA amide (optionally) and was expressed as the sum of the corresponding MHA monomer equivalents in [wt %] or [g] or [mole] or [mole %].

The content of sulfuric acid was determined by alkalimetric titration, the $H_2O_2$ content was determined by a Merck rapid test.

The water content was determined by titration according to Karl-Fischer, the nitrate, sulfite, sulfate and ammonium contents were determined by ion chromatography according to standard methods.

Figure 1:
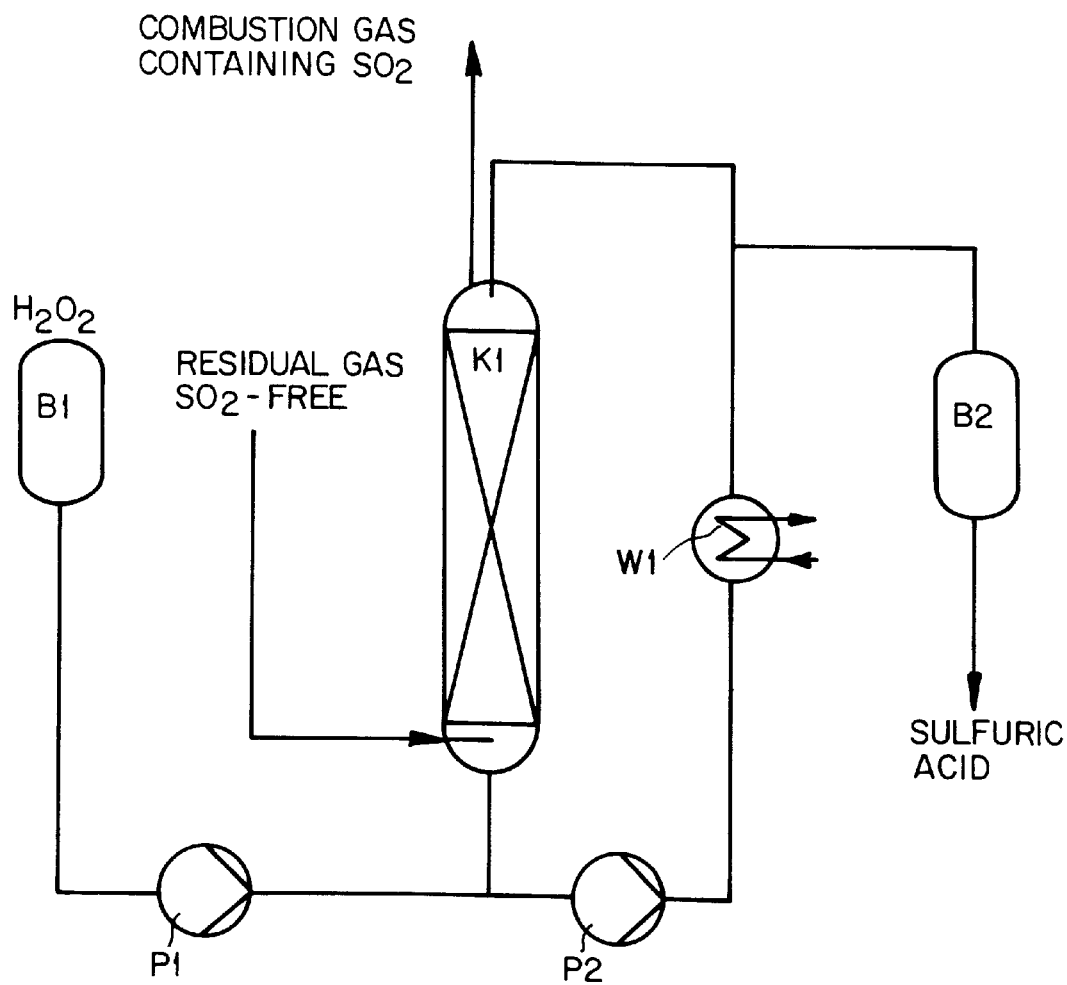
FIG. 1 shows, schematically, apparatus for practicing the invention.
Figure 2:
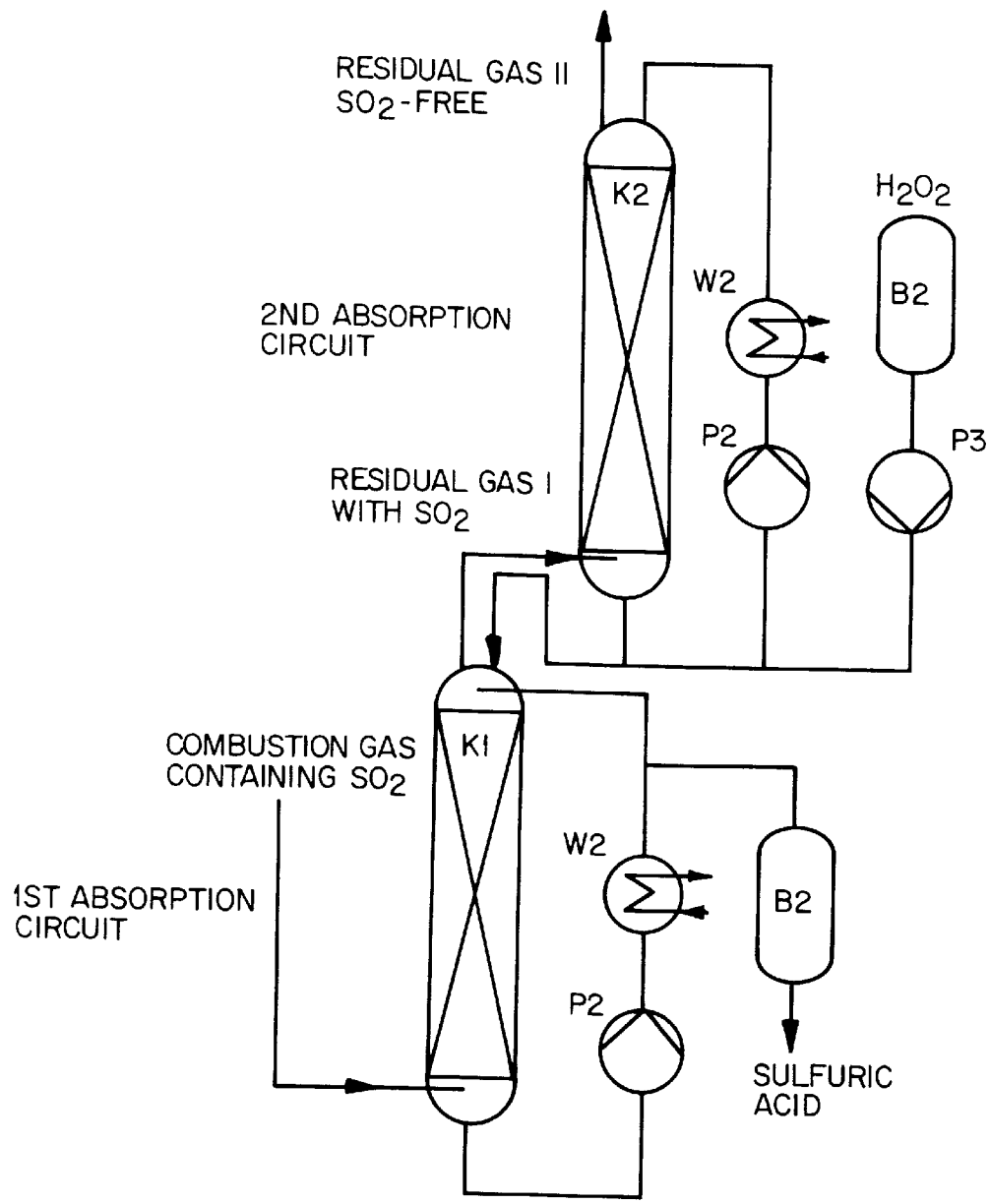
FIG. 2 shows, schematically apparatus for practicing the invention having first and second absorption circuits.
Figure 3:
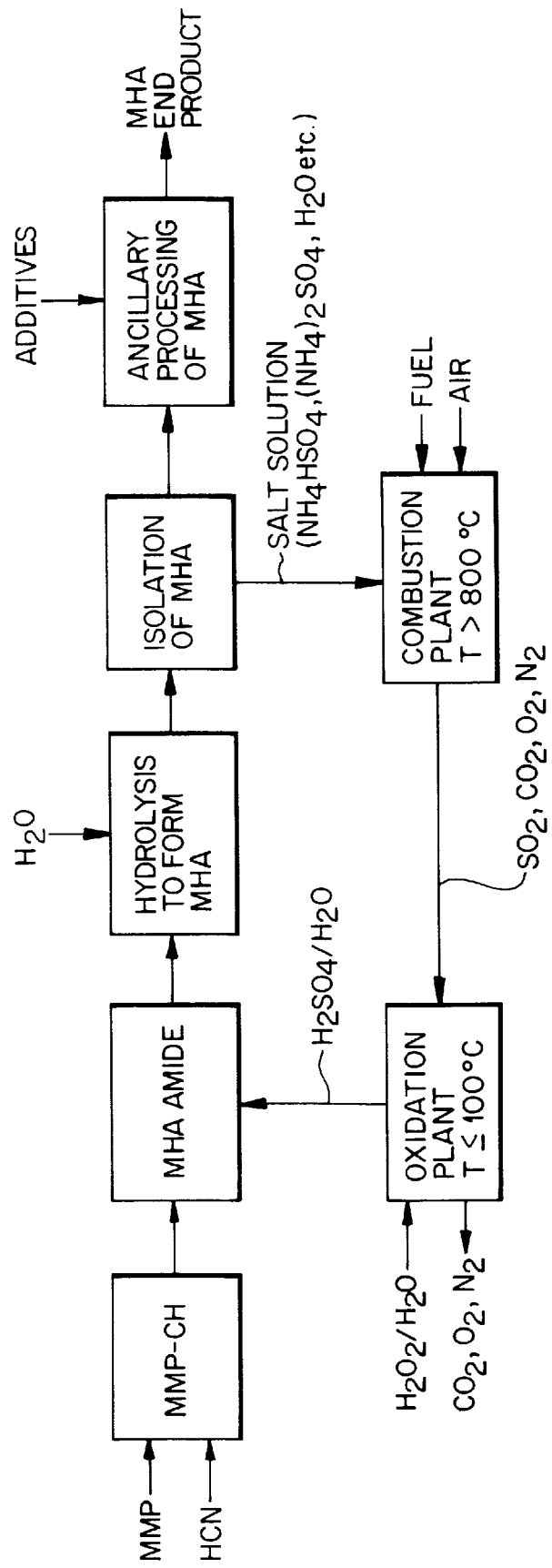
FIGS. 3 shows, schematically, the overall method of the invention.

Description of the Method with Reference to FIG. 1

The schematic structure of the apparatus used for Example 1 is shown in FIG. 1. The apparatus substantially consists of the following parts:

| | |
|---|---|
| Storage tank for hydrogen peroxide | B 1 |
| Receiving tank for sulfuric acid formed | B 2 |
| Metering pump for hydrogen peroxide | P 1 |
| Circulating pump | P 2 |
| Glass absorption column with packings | K 1 |
| Heat exchanger for cooling | W 1 |

The gas mixture, which corresponds in its composition to the crude gas typically resulting from the combustion, was passed at a temperature of 20°–25° C. into the lower part of an absorption column K1 filled with packings. The aqueous sulfuric acid which was formed and which was recycled via the head of the column with the aid of the circulating pump P2 served as an absorption solution. The energy arising in the course of the reaction was captured by the heat exchanger W1, and in this way the temperature in the circuit was limited to a maximum of 3° C. above the gas-inlet temperature. The necessary hydrogen peroxide for the reaction (50 wt % $H_2O_2$) was pumped into the circuit from the storage tank B1 with the aid of the metering pump P1. The excess of $H_2O_2$ in the absorption liquid amounted to max. 10 mole %, relative to the stream of $SO_2$ introduced. The sulfuric acid formed was let off into the receiving tank B2 in a side stream.

EXAMPLE 1

The absorption column was filled with just so much water that the cooling and absorption circuit could be operated safely. 100 l/h of a gas mixture having the composition shown below were introduced into the column. The composition corresponds to that of a typical combustion gas from a combustion furnace for producing $SO_2$ from sulfate-containing raffinate arising from an MHA process:

| 82 vol-% | (3.33 mole/h) | $N_2$ |
| 7 vol-% | (0.28 mole/h) | $CO_2$ |
| 5 vol-% | (0.20 mole/h) | $SO_2$ |
| 6 vol-% | (0.24 mole/h) | $O_2$ |

Addition of the 50 wt % $H_2O_2$ (13.6 g/h, 0.2 mole/h) was effected with low initial feed in a stoichiometric ratio. The gas-inlet temperature amounted to 20° C. The temperature in the cooling circuit did not rise above 23° C. After an interval of several hours the $H_2SO_4$ content in the sulfuric acid flowing off was determined. The $H_2SO_4$ concentration had risen to 74.7 wt %. No loss of hydrogen peroxide could be detected. On average 26 g/h (0.2 mole/h) of a max. 75 wt % $H_2SO_4$ were obtained in the receiving tank B2. The sulfuric acid produced had the following composition:

| Content of $H_2SO_4$ | 74.7 wt % |
| Content of $H_2O$ | 24.85 wt % |
| Content of $SO_3^{2-}$ | 1,570 mg/kg |
| Content of $H_2O_2$ | <0.5 mg/l |
| Content of $NO_3^-$ | <10 mg/kg |

EXAMPLE 2

306 g of 50% hydrogen peroxide (4.5 mole) were provided in the absorption apparatus and pumped in a circuit. At a maximum temperature of 23° C., the gas mixture was introduced for several hours in a manner analogous to Example 1. 596 g of a sulfuric acid resulted, having a content of 74.0 wt % (4.5 mole). No loss of hydrogen peroxide could be detected.

EXAMPLE 3

236 g of 74.7 wt % $H_2SO_4$ (1.8 mole) from Example 1 were submitted in a reaction tank equipped with a stirrer, internal thermometer and reflux condenser. Within 30 min. 403 g (3.0 mole) of 97.7 wt % MMP cyanohydrin were metered into the agitated reactor. The reaction temperature was maintained at 50° C. during the inflow and the subsequent secondary-reaction time of 30 min. When the secondary reaction was over, the reaction mixture was diluted with 540 g water and immediately transferred into a 2-1 Büchi pressure reactor equipped with stirrer and internal temperature-measuring device. The reaction solution had a content of 22.8 wt % MHA amide and 15.3 wt % MHA and, subject to stirring, was heated up to 120° C. and stirred for a further 3 hours at this temperature. After cooling to room temperature, 1,176 g MHA hydrolyzate was isolated having the following composition:

| 0.33 wt % | (0.9% of theor.) | MHA amide |
| 36.26 wt % | (94.6% of theor.) | MHA |
| 1.71 wt % | (about 4.5% of theor.) | MHA dim + oli |
| 38.30 wt % | (100% of theor.) | MHAtot |

256 g (0.663 mole MHA) of the MHA hydrolyzate was extracted twice with 100 ml methyl tert. butyl ether, the organic phases were combined and concentrated by evaporation in a water-jet vacuum. The MHA high concentrate (100 g) primarily produced was diluted with 12 g water and analysed:

| MHAtot | 87.7 wt % | 100 mole-% |
| MHA monomer | 77.2 wt % | 88.0 mole-% |
| MHA dim + oli | 10.5 wt % | 12.0 mole-% |
| $H_2O$ | 12.0 wt % | |
| $SO_4^{2-}$ | 0.2 wt % | |
| $SO_3^{2-}$ | <0.1 wt % | |
| $NO_3^-$ | <10 ppm | |

What is claimed is:

1. A method for recovering sulfuric acid from sulfate salts accumulating in solution or in solid form during sulfuric acid hydrolysis of methylmercaptopropionaldehyde (MMP) cyanohydrin, comprising:

combusting said sulfate salts obtained from the hydrolysis of MMP cyanohydrin in a combustion furnace to produce $SO_2$;

obtaining a gas mixture containing the $SO_2$ produced from said combustion;

passing said gas mixture containing $SO_2$ through an aqueous solution of sulfuric acid and $H_2O_2$;

converting the $SO_2$ contained in said gas mixture into sulfuric acid and recovering said sulfuric acid.

2. The method according to claim 1, wherein the concentration of the hydrogen peroxide is between 10 and 90 wt %.

3. The method according to claim 2, wherein the concentration of the hydrogen peroxide is between 20 and 80 wt %.

4. The method according to claim 2, wherein the concentration of the hydrogen peroxide is between 30 and 60 wt %.

5. The method according to claim 2, wherein the concentrations of the hydrogen peroxide and the $SO_2$ are selected so that a 50 to 78% aqueous sulfuric acid is obtained.

6. The method according to claim 2 wherein the concentrations of the hydrogen peroxide and the $SO_2$ are selected so that a 60 to 75% aqueous sulfuric acid is obtained.

7. The method according to claim 1, wherein during the conversion of $SO_2$ the temperature is between 0° and 100° C.

8. The method according to claim 7, wherein the temperature is between 10° and 80° C.

9. The method according to claim 7, wherein the temperature is between 20° and 60° C.

10. The method according to claim 1, comprising:

carrying out the conversion of $SO_2$ with $H_2O_2$ in apparatus selected from a one-stage apparatus, a two-stage apparatus and a multi-stage apparatus having more than two stages.

11. The method according to claim 1, further comprising:

supplying at least one additional sulfur source to the combustion furnace, wherein said at least one additional sulfur source is selected from the group consisting of sulfur-containing waste gases, sulfur-containing waste waters and sulfur-containing organic wastes.

* * * * *